United States Patent [19]

Lee et al.

[11] Patent Number: 5,597,704
[45] Date of Patent: Jan. 28, 1997

[54] BIOCONVERSION OF CEPHALOSPORIN C TO GLUTARYL-7-AMINOCEPHALOSPORANIC ACID

[75] Inventors: Yun-Huey Lee, Kaohsiung; Wen-Shen Chu, Hsinchu; Wen-Hwei Hsu, Taichung, all of Taiwan

[73] Assignee: Food Industry Research and Development Institute, Taiwan

[21] Appl. No.: 431,962

[22] Filed: May 1, 1995

[51] Int. Cl.$^6$ ............................. C12Q 1/26; C12Q 1/00; C12Q 1/02; C12P 35/00
[52] U.S. Cl. .................. 435/25; 435/4; 435/29; 435/7.31; 435/254.1; 435/255.1; 435/47; 435/49
[58] Field of Search ..................... 435/25, 4, 29, 435/7.31, 34, 254.1, 255.1, 47, 49

[56] References Cited

U.S. PATENT DOCUMENTS

| | | | |
|---|---|---|---|
| 3,658,649 | 4/1972 | Arnold et al. | 435/49 |
| 3,801,458 | 4/1974 | Fildes et al. | 435/25 |
| 3,976,546 | 8/1976 | Smith et al. | 435/25 |
| 4,533,632 | 8/1985 | Smith et al. | 435/47 |
| 5,284,754 | 2/1994 | Bayer et al. | 435/47 |
| 5,296,358 | 3/1994 | Battistel et al. | 435/49 |

OTHER PUBLICATIONS

Isogai et al., "Structure and Expression of cDNA for D–Amino Acid Oxidase Active Against Cephalosporin C from Fusarium Solani", J. Biochem 108:1063–1069, 1990.
Kawamoto et al., "Production of D–Amino Acid Oxidase by Candida Tropicalis", J. Ferment. Technol. 55:13–18, 1977.
Kubicek–Pranz et al., "D–Amino Acid Oxidase from the Yeast Trigonopsis Variabilis", Journal of Applied Biochemistry 7:104–113, 1985.
Lee et al., "Bioconversion of Cephalosporin C with D–Amino Acid Oxidase from the Yeast Rhodosporidium Toruloides", 16:467–472, 1994.
Pollegioni et al., "Purification of Rhodotorula Gracilis D–Amino Acid Oxidase", Protein Expression and Purification 3:165–167, 1992.
Ronchi et al., "The Primary Structure of D–Amino Acid Oxidase from Pig Kidney", The Journal of Biological Chemistry 257:8824–8834, 1982.
Serizawa et al., "Enzymatic Conversion of Cephamycin C By D–Amino Acid Oxidase from Trigonopsis Variabilis", The Journal of Antibiotics 33:585–590, 1980.
Simonetta et al., "Purification and Properties of D–amino-acid Oxidase, an Inducible Flavoenzyme from Rhodotorula Gracilis", Bicchimica et Biophysica Acta 914:136–142, 1987.
Szwajcer et al., "Isolation and Partial Characterization of a D–Amino Acid Oxidase Active Against Cephalosporin C From the Yeast Trigonopsis Variabilis", Biotechnology Letters 7:1–7, 1985.

Primary Examiner—John Kight
Assistant Examiner—Louise N. Leary
Attorney, Agent, or Firm—Fish & Richardson P.C.

[57] ABSTRACT

A method of converting cephalosporin C to glutaryl-7-aminocephalosporanic acid. The method including obtaining a cell preparation from a microorganism which produces D-amino acid oxidase, the preparation being a cell-free extract or a suspension of permeated cells; adding a D-α-amino acid to the preparation; after the adding step, heating the preparation at 50°–75° C. for 5–60 minutes; and incubating cephalosporin C in the preparation. Also disclosed are a method of converting cephalosporin C to glutaryl-7-aminocephalosporanic acid in the absence of exogenous $H_2O_2$, and a method of screening for a D-amino acid oxidase-producing microorganism.

21 Claims, 1 Drawing Sheet

BIOCONVERSION OF CEPHALOSPORIN C TO GLUTARYL-7-AMINOCEPHALOSPORANIC ACID

BACKGROUND OF THE INVENTION

D-amino acid oxidase ("DAO;" EC No. 1.4.3.3 ), which occurs widely in microorganisms as well as in tissues of animals, is known to be able to convert cephalosporin C ("Ceph C"), a D-α-amino acid, to α-ketoadipyl cephalosporanic acid ("α-ketoadipyl 7-ACA"), hydrogen peroxide, and ammonia. α-ketoadipyl 7-ACA, upon reaction with hydrogen peroxide, can be further transformed into glutaryl-7-aminocephalosporanic acid ("GL-7-ACA"). Since GL-7-ACA is a starting material for the production of cephem antibiotics, DAO is of great industrial interest.

SUMMARY OF THE INVENTION

An aspect of this invention relates to a method of converting Ceph C to GL-7-ACA. The method includes the steps of (i) obtaining a cell preparation, i.e., a cellfree extract or a suspension of permeated cells, from a microorganism (e.g., a fungus) which produces DAO; (ii) adding a D-α-amino acid to the cell preparation; (iii) after the adding step, heating the cell preparation at 50°–75° C. for 5–60 minutes (preferably, at 50°–65° C. for 10–40 minutes); and (iv) incubating cephalosporin C in the cell preparation. Apparently, heating of the cell preparation in the presence of D-α-amino acid has no effect on DAO activity but inactivates certain degradable enzymes (e.g., esterases), thereby increasing the conversion rate of Ceph C. After the incubating step, exogenous $H_2O_2$ can be added to the cell preparation for initial conversion or more conversion to GL-7-ACA, if necessary or desirable.

A second aspect of this invention relates to another method of converting Ceph C to GL-7-ACA by first obtaining a cell preparation, a cell-free extract or a suspension of permeated cells, from a microorganism of the Rhodosporidium genus (e.g., *Rhodosporidium toruloides*); and then incubating Ceph C in the cell preparation, thereby producing GL-7-ACA in the absence of exogenous hydrogen peroxide. If desirable, exogenous $H_2O_2$ can be added to the cell preparation for more conversion to GL-7-ACA after the incubating step.

A still further aspect of this invention relates to a method of rapidly screening for microorganism (such as a fungus, e.g., a yeast) which produce DAO. The method includes the steps of (i) growing cells of a target microorganism on the surface of a solid medium (e.g., an agar plate), the medium including a D-α-amino acid as a nitrogen source (i.e., either as the sole or as a major nitrogen source); (ii) permeating the cellular membrane of the grown cells with the vapor of an organic solvent; and (iii) immersing the permeated cells in a solution containing a peroxidase (e.g., EC No. 1.11.1.7) and a redox dye-substrate of the peroxidase (e.g., o-dianisidine, 3,3'-5,5'-tetramethyl-benzidine or 3-amino-9-ethylcarbazole), the substrate being capable of reacting with hydrogen peroxide to form a colored product in a reaction catalyzed by the peroxidase. Preferably, the solution also contains, in addition to a redox dye and a peroxidase, a D-α-amino acid which can be the same as or different from the D-α-amino acid which is used as a nitrogen source to grow the cells. The detection of the colored product, if any, indicates that DAO is present in the microorganism.

Also contemplated within the scope of this invention is a microorganism (e.g., a yeast such as *Rhodosporidium toruloides* or other species of the Rhodosporidium genus) which possesses a DAO activity of 0.8–4.0 IU/mg (e.g., 0.8–1.6, 1.6–2.4, 2.4–3.2, or 3.2–4.0 IU/mg) total cellular protein when grown at 30° C. in a fully aerated medium until the $OD_{660}$ nm nm reading of the medium reaches 7–10 (i.e., the stationary phase), the medium containing a yeast carbon base and 30 mM D-α-Ala as the sole nitrogen source and having a pH of 5.6. Preferably, a cell-free extract or a suspension of permeated cells prepared from the microorganism is capable of converting Ceph C to GL-7-ACA in the absence of exogenous hydrogen peroxide, i.e., the GL-7-ACA/α-ketoadipyl 7-ACA ratio being 0.5 or greater (preferably, 0.7 or greater) in an assay identical to or equivalent to that described in Example 2 or 3 below. Such a microorganism can be identified by the screening method described in the preceding paragraph.

Other features or advantages of the present invention will be apparent from the following drawings and detailed description of several embodiments, and also from the appending claims.

DETAILED DESCRIPTION OF THE INVENTION

Figure 1A:
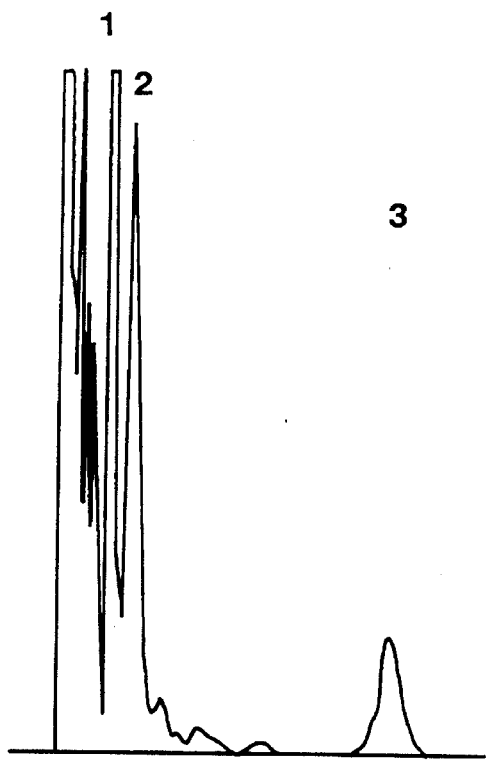
FIG. 1A is an HPLC chromatogram of conversion products of Ceph C by the permeated cells of a *Rhodosporidium toruloides* strain (ATCC 10788) in the absence of exogenous $H_2O_2$.

Cell-free extract or a suspension of permeated cells which is used to convert Ceph C can be prepared from microorganism cells by methods within the scope of a person of ordinary skill in the art. By "permeated cells" is meant cells the membranes of which have been permeated so that Ceph C can enter into the cells to be converted by DAO therein. For an example of how to permeate cells, see Pardee, et al., J. Mol. Biol. 1:165 (1959).

The D-α-amino acid used to practice this invention (either as a nitrogen source to induce the synthesis of DAO, as a stabilizer of DAO in heating treatment, or as a reagent in detecting DAO activity) may contain 3–20 carbons, and preferably, 3–12 carbons (e.g., D-α-Ala, D-α-Met, and D-α-Phe).

The microorganism which can be used to practice this invention or the microorganism of this invention may be a fungus, such as a yeast which belongs to the ascomycete class of fungi. Examples of such a yeast include, but are not limited to, a species of the Saccharomyces genus (e.g., *S. pasteurianus*), the Rhodosporidium genus (e.g., *R. toruloides*), the Rhodotorula genus (e.g., *R. gracilis*), and the Trigonopsis genus (e.g., *T. variabilis*).

3

Without further elaboration, it is believed that one skilled in the art can, based on the description herein, utilize the present invention to its fullest extent. The following specific examples are, therefore, to be construed as merely illustrative, and not limitative of the remainder of the disclosure in any way whatsoever. Any publications cited in this disclosure are hereby incorporated by reference.

EXAMPLE 1

Screening for a microorganism which produces DAO

About 3,000 strains from culture collections and local isolates were screened. Cells from each strain were grown on the YMA medium containing 0.3% yeast extract, 0.3% malt extract, 0.5% peptone, and 2% agar were transferred to a screening medium consisting of 1.17% yeast carbon base (Difco), 0.1% D-α-Ala, and 2% agar.

To further confirm their DAO activity, strains grown on the screening medium at 30° C. for 48 hr and treated with organic solvent vapor such as chloroform for 30–45 min to permeate the cells. A 10 ml solution containing 100 mM D-α-Ala, 0.025% o-dianizidine, and 25 IU peroxidase (EC No. 1.11.1.7) in 100 mM potassium phosphate buffer (pH 8.0) was poured into the plate and incubated at room temperature for 30 min. Cells with DAO activity produced a brownish red zone. Several strains with DAO activity were isolated. $R.$ $toruloides$ (ATCC 10788) showed the highest activity among the isolates.

A single colony of ATCC 10788 grown on the YMA medium was inoculated into 10 ml of medium A consisting of yeast carbon base and 30 mm D-α-Ala at pH 5.6) and incubated at 30° C. and 150 rpm overnight. A 5-ml aliquot of the culture was transferred into 100 ml of medium A and shaken at 150 rpm and 30° C. for 48 hr. When the $OD_{660}$ nm of the cells reached 8.0 (i.e., stationary phase), DAO activities ranging from 0.56 to 0.62 IU/mg total cellular protein were observed. The harvested cells were broken with glass beads and the enzyme activity was measured by the Friedmann method (see Examples 3 and 4 below).

EXAMPLE 2

Conversion of Ceph C in a suspension of permeated cells without preheating treatment ATCC 10788 was grown in a 500 ml Hinton flask containing 50 ml of YMA medium with the following composition: 1% yeast extract, 1.5% malt extract, 0.2% D,L-α-Ala (pH 6.5). The flask was incubated at 30° C. and 150 rpm on a rotary shaker for 48 h when the cells reached the stationary phase. The cells were harvested by centrifugation at 4° C. and 10,000×g for 20 min and used immediately for the preparation of the cell-free extract or permeated cells.

Cells were then suspended in chilled 100 mM potassium phosphate buffer (pH 8.0) containing 2.5% (v/v) toluene in ethanol at 0° C. for 30 min. The permeated cells were washed twice with chilled 100 mM phosphate buffer and then used for the conversion of Ceph C.

The DAO activity toward Ceph C was monitored by HPLC. The reaction mixture contained 30 µl of Ceph C (250 mM), 770 µl of potassium phosphate buffer (100 mM at pH 8.0), and 1.2 ml of permeated cells in a final volume of 2 ml. After incubation at 25° C. for 2 h, 20 µl of $H_2O_2$ (3.5%) was added to the solution and the reaction proceeded for another 10 min at 25° C. The products of conversion in the supernatant were then analyzed by HPLC. The mobile phase was 10% methanol in 20 mM ammonium acetate buffer (pH 4.8). A Nova-Pack C-18 column (Waters Material Synthesis Facility, Taunton), 3.9×150 mm, was used and the UV detector was set at 260 nm. The retention times for Ceph C and GL-7-ACA at a flow rate of 1 ml/min were 2.4 min and 9.5 min, respectively.

Figure 1B:
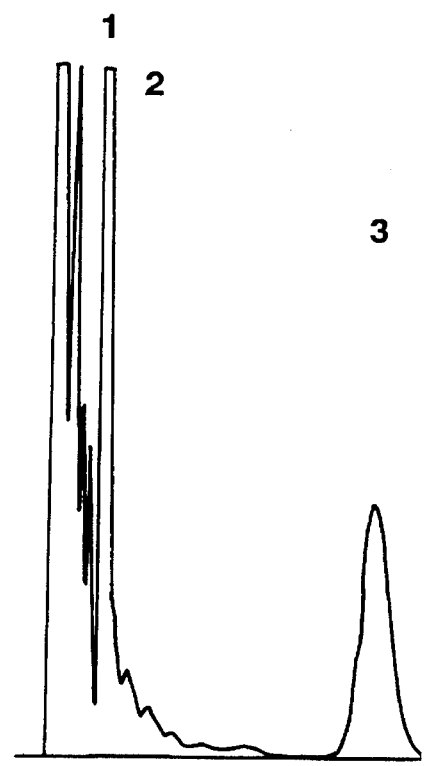
FIG. 1B is an HPLC chromatogram of conversion products of Ceph C by the permeated cells of ATCC 10788 in the presence of exogenous $H_2O_2$.

As shown in FIGS. 1A and 1B, the permeated cells of ATCC 10788 could directly convert a part of Ceph C into GL-7-ACA without the addition of $H_2O_2$ (FIG. 1A). ATCC 10788 was found to contain relatively low catalase activity as compared to that of $T.$ $variabilis$ (data not shown). However, the addition of $H_2O_2$ further transformed the remaining a-ketoadipyl 7-ACA into GL-7-ACA (FIG. 1B). In both FIGS. 1A and 1B, peak 1 stands for Ceph C; peak 2 for a-ketoadipyl 7-ACA; and peak 3 for GL-7-ACA.

EXAMPLE 3

Conversion of Ceph C in a cell-free extract without preheating treatment

Results similar to those shown in FIGS. 1A and 1B were obtained in another experiment, which indicates that a cell-free extract prepared from a ATCC 10788 culture could also convert Ceph C into both α-ketoadipyl 7-ACA and GL-7-ACA in the absence of exogenous $H_2O_2$.

ATCC 10788 was grown in the same manner described in Example 2 above. The cell-free extract was prepared as follows: Cell paste of the ATCC 10788 culture was suspended in 100 mM potassium phosphate buffer (pH 8.0) containing 2 mM EDTA, 5 mM 2-mercaptoethanol and 0.1% (v/v) Triton X-100 and shaken vigorously with glass beads of 0.45–0.55 mm diameter for five periods of 1 min with 1 min interval at 4° C. The tubes were placed on ice during these idle intervals. The homogenate was centrifuged at 21,000×g for 30 min and the supernatant was collected for Ceph C conversion or enzyme assay.

The reaction mixture contained 2 ml of Ceph C (250 mM), 7 ml of potassium phosphate buffer (100 mM at pH 8.0), and 1.0 ml of cell-free extract in a final volume of 10 ml. After incubation at 37° C. for 1 h, 105 µmoles of α-ketoadipyl 7-ACA and 75 µmoles of GL-7-ACA were obtained. Upon addition of 150 µl of $H_2O_2$ (3.5%), all of the α-ketoadipyl 7-ACA was converted to GL-7-ACA. The quantitative data were obtained by HPLC in a manner analogous to that described in Example 2 above. More specifically, the mobile phase was 10% methanol in 20 mM ammonium acetate buffer (pH4.8). A Nova-Pack C-18 column (Waters Material Synthesis Facility, Taunton), 15×0.46 cm, was used and the UV detector was set at 260 nm. The flow rate was 1 ml/min.

EXAMPLE 4

Conversion of Ceph C in a suspension of cell-free extract with preheating treatment The cell-free extract from ATCC 10788 was prepared in the same manner described in Example 3 above.

DAO activity was assayed by measuring the productivity of keto acid according to the method of Freidemann, Methods Enzymol. 3:414 (1957). The reaction mixture contained 100 mM D-α-Ala, 100 mM potassium phosphate buffer (pH 8.0), 400 IU of bovine liver catalase, and an appropriate amount of enzyme in a final volume of 1 ml. After incubation at 37° C. for 15 min, the keto acid produced was determined by a colorimetric assay using 2,4-dinitrophenylhydrazine and compared against the standard curve for pyruvic acid. One unit (IU) of DAO activity corresponds to the formation of 1 µmole of keto acid per min at 37° C.

ATCC 10788 was shown to possess high esterase activity (data not shown) which might give rise to unknown side products appeared before peak 1 in Ceph C conversion (FIGS. 1A and 1B). Ceph C or D-α-Ala was used to raise the thermal tolerance of DAO in a heating treatment of the cellfree extract aimed at inactivating undesirable degradative enzymes such as esterases. Less than half of the DAO activity in the cell extract containing Ceph C was lost after heating at 55° C. for 5 min. No activity could be detected after repeating the same treatment for five times. On the other hand, no loss of DAO activity was observed after heat treatment in the presence of 100 mM D-α-Ala. The results were summarized in Table 1 below:

TABLE 1

Thermostability of DAO in the presence of a substrate

| Cell extract in | Relative activity(%)[a] | |
| --- | --- | --- |
| | Treatment 1[b] | Treatment 2[c] |
| Phosphate buffer (pH 8.0) | 4 | 3 |
| Phosphate buffer (pH 8.0) | | |
| +100 mM Ceph C | 56 | 0 |
| +100 mM D-α-Ala | 100 | 100 |

[a]Enzyme activity before treatment was 100%.
[b]Heated at 55° C. for 5 min.
[c]Heated repeatedly at 55° C. for 5 min for five cycles, each with 1-min interval on ice.

The results indicated that the thermal tolerance of DAO could be greatly enhanced by the presence of Ceph C or D-α-Ala. D-α-Ala was particularly effective in protecting DAO during heat treatment. The lesser effect of Ceph C is believed to be due to thermal lability of that compound.

Figure 2A:
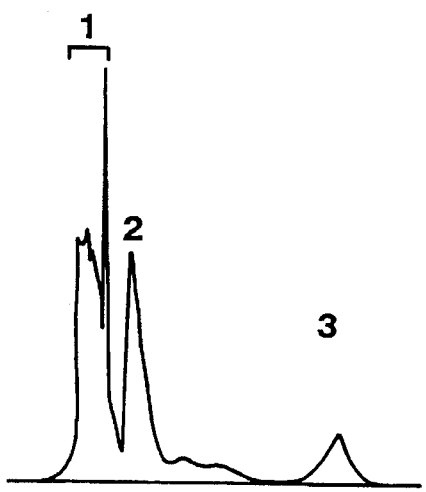
FIG. 2A is an HPLC chromatogram of conversion products of Ceph C by the cell-free extract of ATCC 10788 in the presence of exogenous $H_2O_2$ without heat treatment.
Figure 2B:
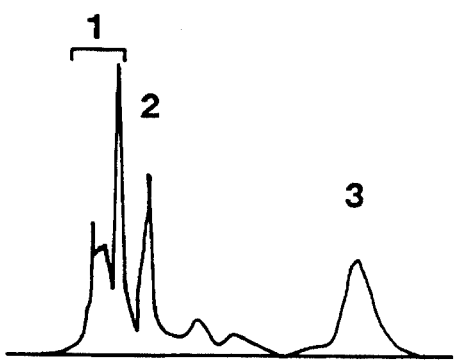
FIG. 2B is an HPLC chromatogram of conversion products of Ceph C by the cell-free extract of ATCC 10788 in the presence of exogenous $H_2O_2$ with heat treatment.

It was further observed that the side products formed during Ceph C conversion with the D-α-Ala/preheated cell extract were substantially decreased and the yield of GL-7-ACA was higher than that of untreated cell extract (compare FIG. 2A with FIG. 2B). More specifically, shown in FIGS. 2A and 2B are HPLC chromatograms of the products of Ceph C conversion by untreated cell extract (FIG. 2A), and by the cell extract repeatedly heated at 55° C. for 5 min for five cycles, each with 1-min interval on ice (FIG. 2B); exogenous $H_2O_2$ was added after the conversion of Ceph C in both experiments. In each of FIGS. 2A and 2B, peaks 1 stand for unknown side products, peak 2 stands for Ceph C, and peak 3 stands for GL-7-ACA. The HPLC assay was performed in a manner identical to that described in Example 2 above.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims. For example, conversion of a D-α-amino acid analogue of Ceph C in manners similar or identical to those described in Examples 2–4 is also within the scope of this invention under the doctrine of equivalents.

What is claimed is:

1. A method of converting cephalosporin C to glutaryl-7-aminocephalosporanic acid, the method comprising:
   obtaining a cell preparation from a microorganism which produces D-amino acid oxidase (EC No. 1.4.3.3), said cell preparation being a cell-free extract or a suspension of permeated cells;
   adding a D-α-amino acid to said cell preparation;
   after the adding step, heating said cell preparation at 50°–75° C. for 5–60 minutes; and
   incubating cephalosporin C in said cell preparation.

2. The method of claim 1, wherein said cell preparation is a cell-free extract.

3. The method of claim 2, wherein said cell preparation is heated at 50°–65° C. for 10–40 minutes.

4. The method of claim 3, wherein said microorganism is a fungus.

5. The method of claim 4, wherein said microorganism is a yeast.

6. The method of claim 5, wherein said microorganism is of the Rhodosporidium genus.

7. The method of claim 6, wherein said microorganism is *Rhodosporidium toruloides*.

8. The method of claim 1, wherein said cell preparation is a suspension of permeated cells.

9. The method of claim 8, wherein said cell preparation is heated at 50°–65° C. for 10–40 minutes.

10. The method of claim 9, wherein said microorganism is a fungus.

11. The method of claim 10, wherein said microorganism is a yeast.

12. The method of claim 11, wherein said microorganism is of the Rhodosporidium genus.

13. The method of claim 12, wherein said microorganism is *Rhodosporidium toruloides*.

14. A method of converting cephalosporin C to glutaryl-7-aminocephalosporanic acid, said method comprising:
   obtaining a cell preparation from a microorganism of the Rhodosporidium genus, said cell preparation being a cell-free extract or a suspension of permeated cells; and
   incubating cephalosporin C in said cell preparation, whereby producing glutaryl-7-aminocephalosporanic acid in the absence of exogenous hydrogen peroxide.

15. The method of claim 14, wherein said cell preparation is a cell-free extract.

16. The method of claim 15, wherein said microorganism is *Rhodosporidium toruloides*.

17. The method of claim 14, wherein said cell preparation is a suspension of permeated cells.

18. The method of claim 17, wherein said microorganism is *Rhodosporidium toruloides*.

19. A method of determining the presence of D-amino acid oxidase (EC No. 1.4.3.3) in a microorganism, said method comprising:
   growing cells of said microorganism on the surface of a solid medium, said medium including a D-α-amino acid as a nitrogen source;
   permeating the cellular membrane of said grown cells with the vapor of an organic solvent; and
   immersing said permeated cells in a solution containing a peroxidase and a substrate of said peroxidase, said substrate being capable of reacting with hydrogen peroxide to form a colored product in a reaction catalyzed by said peroxidase;
   wherein the detection of said colored product, if any, indicates that D-amino acid oxidase (EC No. 1.4.3.3) is present in said microorganism.

20. The method of claim 19, wherein said solution further contains a D-α-amino acid.

21. The method of claim 20, wherein said microorganism is a fungus.

* * * * *